United States Patent
Grudin et al.

(10) Patent No.: US 7,503,689 B2
(45) Date of Patent: Mar. 17, 2009

(54) MEASURING AND TRIMMING CIRCUIT COMPONENTS EMBEDDED IN MICRO-PLATFORMS

(75) Inventors: Oleg Grudin, Montreal (CA); Leslie M. Landsberger, Westmount (CA)

(73) Assignee: Microbridge Technologies Inc., Montrëal, Quëbec (CA)

( * ) Notice: Subject to any disclaimer, the term of this patent is extended or adjusted under 35 U.S.C. 154(b) by 0 days.

(21) Appl. No.: 11/878,356

(22) Filed: Jul. 24, 2007

(65) Prior Publication Data

US 2007/0263697 A1 Nov. 15, 2007

Related U.S. Application Data

(63) Continuation of application No. 11/232,909, filed on Sep. 23, 2005, now Pat. No. 7,261,461.

(60) Provisional application No. 60/612,156, filed on Sep. 23, 2004.

(51) Int. Cl.
*G01K 15/00* (2006.01)
*G01K 7/00* (2006.01)
*H01C 10/00* (2006.01)

(52) U.S. Cl. .................. 374/1; 374/185; 374/183; 338/195

(58) Field of Classification Search ........ 338/195; 374/1, 185, 183

See application file for complete search history.

(56) References Cited

U.S. PATENT DOCUMENTS

| | | | |
|---|---|---|---|
| 2003/0178396 A1* | 9/2003 | Naumov et al. | 219/121.69 |
| 2004/0239477 A1* | 12/2004 | Landsberger et al. | 338/195 |
| 2006/0049912 A1* | 3/2006 | Grudin et al. | 338/195 |
| 2006/0279349 A1* | 12/2006 | Grudin et al. | 327/334 |

FOREIGN PATENT DOCUMENTS

JP 63164354 A * 7/1988

\* cited by examiner

*Primary Examiner*—Gail Verbitsky
*Assistant Examiner*—Mirellys Jagan
(74) *Attorney, Agent, or Firm*—Ogilvy Renault, LLP (57) ABSTRACT

There is described a method and sub-circuit to measure temperature coefficients (coefficient of variation of a measurable parameter of the component), by using a thermally-isolated silicon micro-platform with a mass of mono-crystalline silicon suspended from it. The particular effectiveness of the measurement of temperature coefficient(s) stems from the influence of the mono-crystalline silicon mass in maintaining a substantially uniform temperature throughout the micro-platform. The measurement of temperature coefficient can be an absolute temperature coefficient of one or more components, or can be a relative temperature coefficient of two components, or can be relative temperature coefficients between more than two components.

8 Claims, 4 Drawing Sheets

FIGURE 1A mono-crystalline silicon mass

MEASURING AND TRIMMING CIRCUIT COMPONENTS EMBEDDED IN MICRO-PLATFORMS

CROSS-REFERENCE TO RELATED APPLICATIONS

This application is a continuation of U.S. patent application Ser. No. 11/232,909, filed on Sep. 23, 2005 now U.S. Pat. No. 7,261,461 which claims priority of U.S. Provisional application 60/612,156 filed on Sep. 23, 2004.

TECHNICAL FIELD

The present application relates to the field of thermally trimmable devices both passive and/or active, including more specifically, thermally trimmable electronic components, including thermally-trimmable resistors, embedded in thermally-isolated micro-platforms.

BACKGROUND OF THE INVENTION

Thermally-isolated circuit elements have been developed and made in several ways. Reay et al. (U.S. Pat. No. 5,600,174) have shown that electrochemical etching of silicon can be used to create small masses of thermally-isolated silicon, in which circuit components could be housed. Such thermally-isolated circuit elements have the advantage that they can be heated independently of nearby circuit elements on the same chip or substrate. In this way, their operating temperature can be controlled independently without affecting the operation of other nearby circuit elements.

Grudin et al (WO2003/023794) have shown that resistors embedded in microstructures made of typical surface films used in integrated circuit fabrication processes, could enable thermal trimming of those resistors.

In electronics and microelectronics, especially analog electronics and microelectronics, the behavior of electronic components and circuits under conditions of varying temperatures is a very important topic. Circuit components are prone to significantly varying temperature coefficients with non-zero tolerances from as-manufactured specifications. As a result, electronic system designers, and analog microelectronics designers must take great efforts to design circuits to be relatively robust to temperature variations during operation.

Testing and characterization of the temperature behavior of such circuits in volume manufacturing or assembly is not trivial. Circuit parameters must be measured at room temperature, and also measured at least at one other temperature. Significant cost (time, resources) arises from the fact that the circuit must be heated and cooled, as well as stabilized at the measurement temperatures, and this typically consumes a significant amount of time.

SUMMARY OF THE INVENTION

An embodiment of the present invention measures temperature coefficients (coefficient of variation of a measurable parameter of the component), by using a thermally-isolated silicon micro-platform with a mass of mono-crystalline silicon suspended from it. The particular effectiveness of the measurement of temperature coefficient(s) stems from the influence of the mono-crystalline silicon mass in maintaining a substantially uniform temperature throughout the micro-platform. The measurement of temperature coefficient can be an absolute temperature coefficient of one or more components, or can be a relative temperature coefficient of two components, or can be relative temperature coefficients between more than two components.

Another embodiment of the present invention trims a thermally-trimmable resistance such that its trimming performance benefits from the substantially uniform temperature distribution provided by the mono-crystalline silicon mass.

Another embodiment of the present invention measures (a) parameter(s) of a plurality of electronic components such that their relative temperature coefficients can be effectively measured, even though their materials, geometry, and thermal conduction properties may be significantly different. For example one can measure the relative tempco of a polysilicon resistor embedded in the surface dielectric films of the micro-platform vs. a diffused resistor embedded in the mono-crystalline mass.

Another embodiment of the present invention comprises an integrated circuit or sub-circuit in a silicon substrate, where the integrated circuit or sub-circuit includes certain components (including thin-film resistors, diffused resistors, and other passive or active devices such as transistors or diodes), where one or more of those certain components is/are sensitive to temperature, and whose temperature-induced variation significantly influences the output of the integrated circuit or sub-circuit, such that heating the component would result in temperature-induced shift of said output, and such that measurement of said shift would result in an estimate of the temperature coefficient of said output.

Another embodiment of the present invention comprises active circuit elements, along with trimmable resistors, such that the combination can be temperature-conditioned (tempco-measured and tempco-adjusted).

Another embodiment of the present invention comprises an integrated circuit or sub-circuit in a silicon substrate, where the integrated circuit or sub-circuit includes diffused resistors and active devices such as transistors and diodes, and is tempco-trimmable without requiring heating of the whole substrate.

Another embodiment of the present invention comprises an integrated circuit or sub-circuit in a silicon substrate, where the integrated circuit or sub-circuit includes at least one thermally-trimmable thin-film (e.g. polysilicon) resistor, as well as at least one diffused resistor in the mono-crystalline mass, and where the thermally-trimmable resistor can be tempco-trimmed with respect to the diffused-resistor, because they are at the same temperature and therefore their relative tempco can be measured.

In accordance with a first broad aspect of the present invention, there is provided a method of determining a temperature coefficient of a parameter of a circuit, the method comprising: providing a thermally-isolated micro-platform on a substrate, the micro-platform having at least a dielectric layer and a conductive layer; maintaining a substantially uniform temperature throughout the micro-platform by providing said thermally-isolated micro-platform with a mass of mono-crystalline silicon suspended beneath it and above a cavity in the substrate; embedding at least one resistor in the thermally-isolated micro-platform; measuring the parameter of the circuit at a first temperature and a second temperature by applying heat pulses to locally heat the portion of the micro-platform which contains the mono-crystalline silicon mass; and determining the temperature coefficient based on the measured values.

The heating resistor is a resistor that is subjected to an electric signal such that it dissipates power for the purpose of heating either itself, or another component placed nearby that will benefit from the heat injected into the heating resistor.

The silicon mass on the bottom of the micro-platform provides better thermal uniformity when measuring a temperature coefficient of a parameter of the circuit. The temperature coefficient can be absolute or relative (i.e. between two components in the circuit).

In a preferred embodiment, additional components are also embedded into the micro-platform. These additional components can be active devices, such as diodes or transistors embedded in the silicon mass, passive devices such as diffused resistors embedded in the silicon mass, or active and passive devices embedded in the dielectric layers, such as a capacitor, a metal trace embedded between the dielectric layers, a polysilicon gate of a Field Effect Transistor, or a thin-film transistor.

Additionally, the parameter being measured can be the output of the circuit. In this case, a heating resistor or an adjacent component embedded in the thermally-isolated micro-platform can be a temperature-sensitive component which is critical to the temperature variation of the circuit, ("heat-critical" for short), meaning that heating it, and measuring the output of the circuit, is enough to predict the output of the circuit at the same elevated temperature. The first temperature can be room temperature, while the second temperature is an elevated temperature resulting from the heat pulses applied to the heating resistor. If there is enough room on the micro-platform, the entire circuit may be embedded in it.

In accordance with a second broad aspect of the present invention, there is provided a method for adjusting a temperature coefficient of a parameter of a circuit, the method comprising: providing a thermally-isolated micro-platform on a substrate, the micro-platform having at least a dielectric layer, a conductive layer, and a mass of mono-crystalline silicon suspended beneath it and above a cavity; embedding at least one thermally trimmable component in the thermally-isolated micro-platform; applying local heat pulses to the at least one component to thermally trim the parameter of the circuit; and measuring the temperature coefficient of the parameter of the circuit, and repeating the applying until a desired value for the temperature coefficient of the parameter of the circuit has been reached.

The thermally trimmable component can be a resistor that is thermally trimmable and self-heating, which means the heat pulses are applied directly to the trimmable resistor, or there can be a heating resistor also embedded in the micro-platform used for heating and trimming the trimmable component. Having the silicon mass underneath the micro-platform provides better temperature uniformity and also allows temperature-stabilizing at an intermediate elevated temperature, so that the circuit is less prone to variations in ambient temperature.

Embedded in the micro-platform can be the entire circuit, or only part of the circuit. This can include diodes, transistors, diffused resistors, thin-film resistors, capacitors, metal traces, etc. Trimming can be done of the resistance value of the thermally trimmable resistor, of the temperature coefficient of resistance of the thermally trimmable resistor, of the relative temperature coefficient between a thermally trimmable resistor and any other component embedded in the micro-platform (because they are at the same temperature), of the temperature coefficient of the output of the circuit, etc.

Additionally, the thermal budget of an active device embedded in the micro-platform can be changed by applying heat through the heating resistor, since the devices can be thus annealed in-situ. Annealing the active devices that are part of the circuit in-situ can also allow trimming of the temperature coefficient of the output of the circuit.

In accordance with a third broad aspect of the present invention, there is provided a sub-circuit for determining a temperature coefficient of a parameter of a circuit, the sub-circuit comprising: a thermally-isolated micro-platform on a substrate, the micro-platform having at least a dielectric layer, a conductive layer, and a mass of mono-crystalline silicon suspended beneath it and above a cavity; at least one heating resistor embedded in the thermally-isolated micro-platform; heating circuitry for applying local heat pulses to the resistor to elevate the temperature of the sub-circuit to a plurality of temperatures; measuring circuitry for measuring the parameter at the plurality of temperatures and determining the temperature coefficient(s) (linear and optionally non-linear), of the parameter based on measured values at the plurality of temperatures.

As in the case of the method for measuring described above, the micro-platform may be embedded with a plurality of different components, ranging from a part of the circuit to the entire circuit. The heating circuitry applies the heat pulses to the heating resistor, thus elevating its temperature such that a measurement can be taken. Improved temperature uniformity is obtained thanks to the mass of silicon on the micro-platform. Heating circuitry and measuring circuitry can be as described in WO2004/083840, which is hereby incorporated by reference. The heating and measuring circuitry can be on-chip or off-chip.

In accordance with a fourth broad aspect of the present invention, there is provided a sub-circuit for adjusting a temperature coefficient of a parameter of a circuit, the sub-circuit comprising: a thermally-isolated micro-platform on a substrate, the micro-platform having at least a dielectric layer, a conductive layer, and a mass of mono-crystalline silicon suspended beneath it and above a cavity; at least one thermally trimmable component embedded in the thermally-isolated micro-platform, heating circuitry for applying local heat pulses to the component to thermally trim the component and thereby adjust the temperature coefficient of the parameter of the circuit; and measuring circuitry for measuring the temperature coefficient of the parameter and determining the temperature coefficient of the parameter based on the measured values.

In accordance with a fifth broad aspect of the present invention, there is provided a method of compensating for temperature variations in a temperature-sensitive portion of a circuit, the method comprising: embedding said temperature-sensitive portion of said circuit in a suspended mass of mono-crystalline silicon beneath a thermally-isolated micro-platform on a substrate; temperature conditioning said circuit by measuring an output of said circuit while unheated, heating said temperature-sensitive portion to imitate heating of said circuit, thereby causing temperature variations in said temperature-sensitive portion, and measuring said output of said circuit during said heating, determining a temperature drift of said circuit due to said heating; calculating a desired trim of said circuit to compensate for said temperature drift; and trimming a part of said circuit.

In accordance with a sixth broad aspect of the present invention, there is provided a method for measuring a relative temperature coefficient of a parameter of two components having different geometries, the method comprising: providing at least one thermally-isolated micro-platform on a substrate, the micro-platform having at least a dielectric layer, a conductive layer, and a mass of mono-crystalline silicon suspended beneath it and above a cavity in the substrate; embedding a first component having a first geometry in said micro-platform; embedding a second component having a second geometry different from said first geometry in said micro-platform; maintaining a substantially equivalent temperature distribution for said first component and said second component by applying a series of heat pulses to locally heat a portion of said micro-platform which contains the mono-crystalline silicon mass; measuring said parameter at a first temperature and a second temperature; and determining the relative temperature coefficient based on measured values of said parameter.

In accordance with a seventh broad aspect of the present invention, there is provided a method of trimming a parameter of a component in a circuit, the method comprising: providing a thermally-isolated micro-platform on a substrate, the micro-platform having at least a dielectric layer, a conductive layer, and a mass of mono-crystalline silicon suspended beneath it and above a cavity in the substrate; embedding said component in the mass of mono-crystalline silicon; applying local heat pulses to the component to thermally trim the parameter; and measuring the parameter and repeating the applying until a desired value for the parameter has been reached.

As described above, many components can be embedded into the micro-platform and trimming can be of absolute temperature coefficient, or relative temperature coefficient, as in relative between two or more embedded components. The heating circuitry and measuring circuitry may be as described in WO 2004/097860, which is hereby incorporated by reference. The heating and measuring circuitry can be on-chip or off-chip.

The term "tempco" is to be understood as an abbreviation of "temperature coefficient". The terms "island" and "silicon island" are to be understood as referring to a thermally-isolated micro-platform on a substrate, the micro-platform having at least a dielectric layer, a conductive layer, and a mass of mono-crystalline silicon suspended beneath it and above a cavity. The term "conductive layer" is to be understood as referring to a resistive or conductive layer, as opposed to an insulating layer, such as are implemented by dielectrics in suspended microstructures herein. Thin film resistors are implemented in such a "conductive layer".

BRIEF DESCRIPTION OF THE DRAWINGS

Further features and advantages of the present invention will become apparent from the following detailed description, taken in combination with the appended drawings, in which:

FIG. 1b shows the corresponding cross-sectional view through the line x-x in FIG. 1a.

FIG. 1c shows the corresponding cross-sectional view through the line y-y in FIG. 1a.

DETAILED DESCRIPTION OF THE PREFERRED EMBODIMENT

Creation of Released Microstructure with Hanging Silicon Island: Islands of silicon suspended beneath microstructure films have been realized in the prior art. For example, Reay et al (U.S. Pat. No. 5,600,174) implemented active devices in such islands made by electrochemically-controlled wet silicon etching in the mid-1990's. Also, Baltes et al (Ref: "Digital MOS-Transistor-Based Microhotplate Array for Simultaneous Detection of Environmentally Relevant Gases", M. Graf, S. Taschini, P. Kaser, C. Hagleitner, A. Hierlemann, H. Baltes in the Proceedings of the MEMS 2004 Conference in Maastricht, January, 2004 p. 351), have recently published devices made by pn-junction electrochemically-controlled etch stop methods.

Figure 1A:
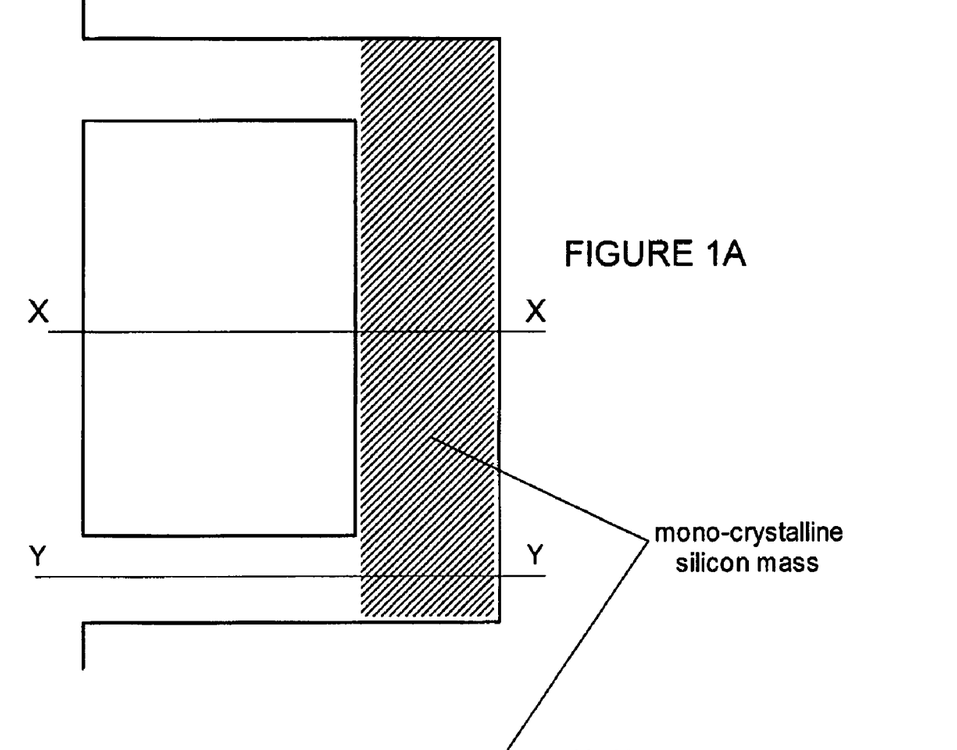
FIG. 1a shows schematically a top view of a generic mono-crystalline silicon mass adhering beneath a microstructure patterned in dielectrics.
Figure 1B:
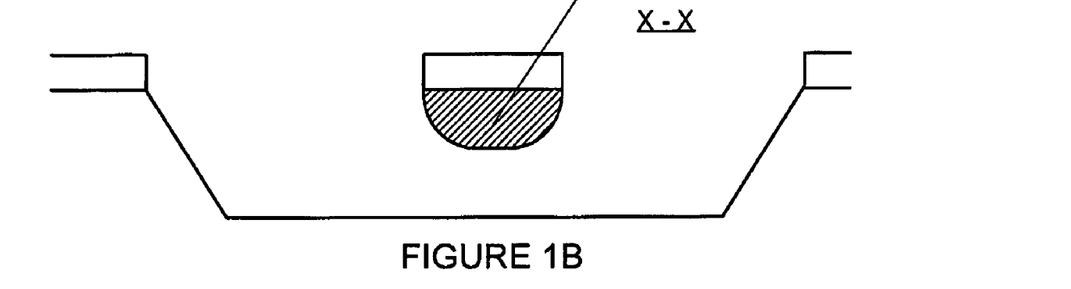
Figure 1C:
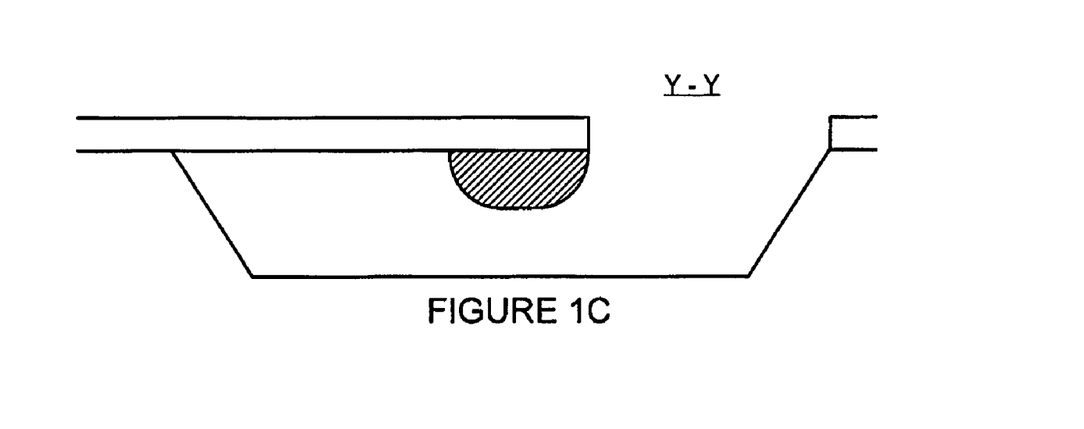
Figure 2A:
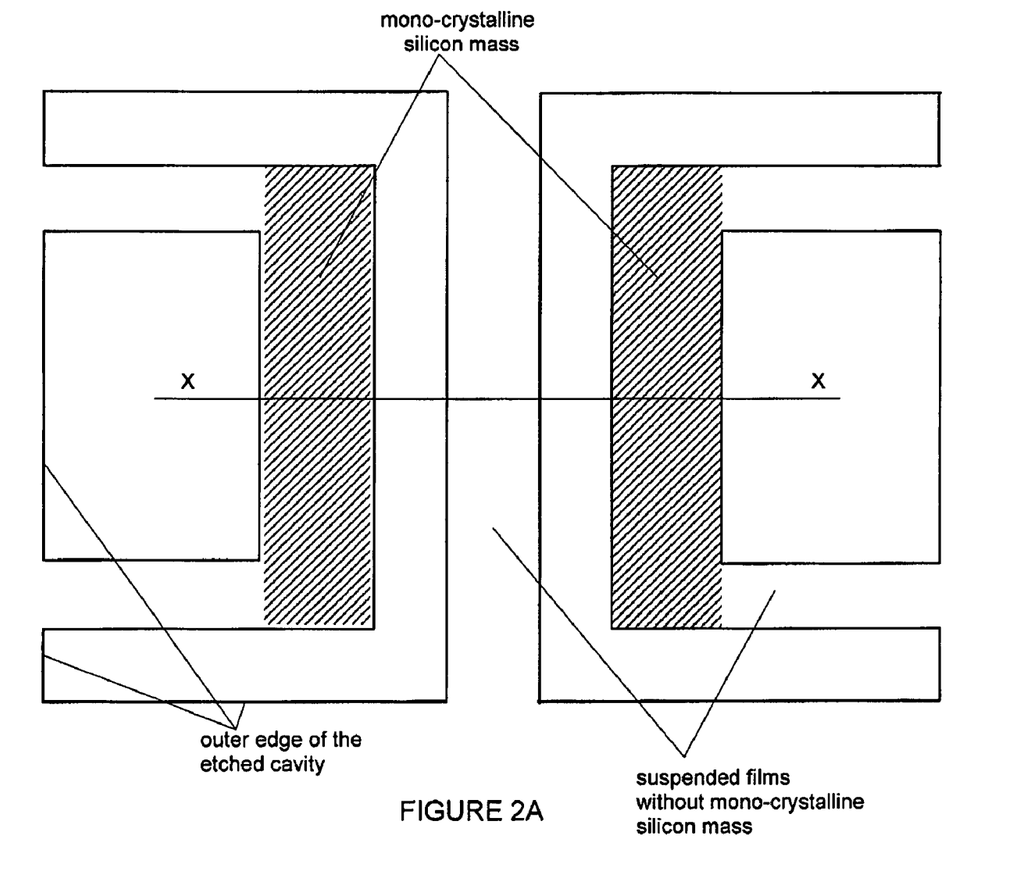
FIG. 2a shows schematically a top view of a set of three suspended microstructures patterned in dielectrics. The two cantilever-shaped microstructures are symmetrically shaped and positioned about the central microstructure.
Figure 2B:
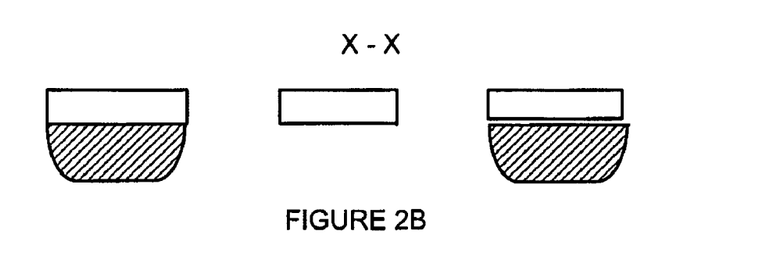
FIG. 2b shows the corresponding cross-sectional view through the line x-x in FIG. 2a, showing that the outer two of the three microstructures have mono-crystalline silicon masses hanging beneath them.

A preferred embodiment of the present invention consists of a thermally-isolated micro-platform, which includes a mono-crystalline silicon mass (instead of simply dielectric films with embedded conductors). In this case, there would remain a thermally-isolated block of silicon adhering beneath the suspended films, an embodiment of which is depicted in FIG. 1. FIG. 1a illustrates a simple embodiment in which a cantilever structure is provided, and a portion of the structure has a silicon mass underneath. A cross-sectional view of that portion along line x-x is shown in FIG. 1b. A cross-sectional view of the portion along line y-y is shown in FIG. 1c. Such structures can be made by many typical processes known in the field of etching and micro-fabrication.

Creation of a silicon island, such as described above, can be used to obtain better thermal uniformity for tempco-measureable and/or thermally-trimmable components, (such as thermally-trimmable resistors), provided one can tolerate slower trimming time (since the thermal inertia will be greater with the mono-crystalline silicon present attached to the dielectric layers).

The thermal conductivity of mono-crystalline silicon is approximately 1 W/cm·K, significantly (almost an order of magnitude) greater than that of polysilicon, and two orders of magnitude greater than that of silicon dioxide. If the mono-crystalline silicon slab is 10 μm thick, and the polysilicon is typically ~0.3 μm, then the heat distribution (and therefore temperature uniformity) will be much more effective with a mono-crystalline slab of silicon as part of the thermally-isolated micro-platform than without it.

Note that, on the other hand, the thermal inertia of the additional slab of silicon does not increase the total thermal inertia of the micro-platform prohibitively. If one assumes that the dielectric layers (and embedded conductors) have a total thickness of approximately 5 μm, and that the mono-crystalline silicon slab is approximately 10 μm, this may have the effect of roughly doubling the overall thermal inertia of the structure. This would roughly double the temperature rise and fall times during tempco measuring and trimming.

The enhanced thermal uniformity allows improvement in measurement of temperature coefficient of resistance since the resistance to be measured will be at a more homogeneous temperature, especially during measurement at one or more elevated temperatures while heating by a heating element.

Note that even a single resistor positioned in such a silicon island is a useful structure, since it can be used to heat itself, and since the rest of the island will serve to make the temperature distribution more uniform, and therefore the resistance of the single resistor can be measured at several temperatures, allowing calculation (estimation) of the temperature coefficient of resistance (linear and higher order, if at least three temperatures are used). Note that this single heater resistor can be a thin-film (e.g. polysilicon) resistor embedded in the dielectrics, or can be embedded in the mono-crystalline silicon (e.g. as a diffused resistor).

Other circuit components can also be positioned in the silicon island for measurement of absolute or relative temperature coefficient of a parameter of that component. If a heating resistor is positioned in the island, it can be used to heat the other components to the elevated temperatures needed for the measurement.

If the absolute temperature coefficient of the component is desired, then a means of measuring the temperature is required. This can be realized by either calibrating the temperature-vs-voltage or temperature-vs-current characteristics of the heating-resistor itself, or (especially if the heating resistor itself is prone to drift over time and use), addition of a separate temperature-sensing component, such as another resistor with known and non-zero TCR, or a pn-junction-based temperature sensor.

Figure 4:
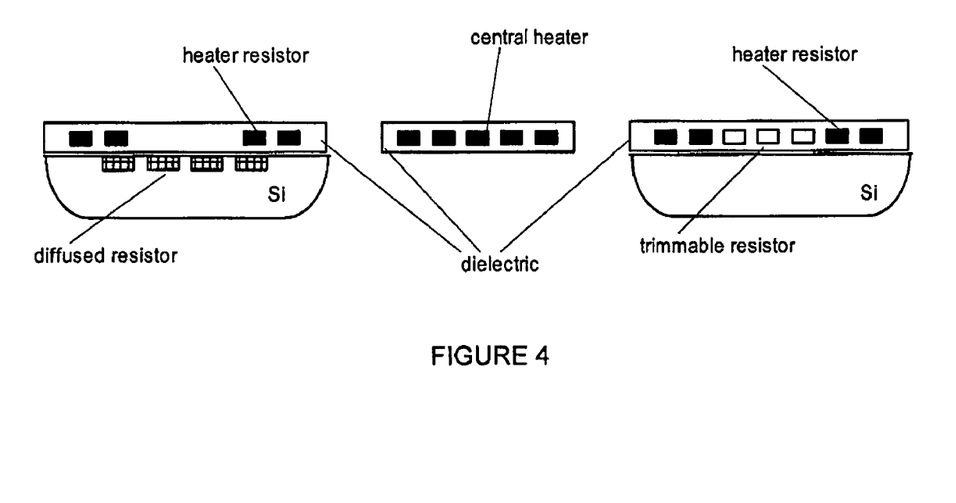
FIG. 4 shows two micro-platforms with sub-circuits embedded therein and a central heater positioned between the two micro-platforms, and is a more detailed version of the cross-section diagram in FIG. 2b.

An example of measurement of temperature coefficient that is enabled by the invention is the measurement of relative temperature coefficient of a thin-film (e.g. polysilicon) resistor embedded within the dielectrics, vs. a diffused resistor embedded within the mono-crystalline mass, as is illustrated in FIG. 4. In this case, even though the two components are made of different materials having different heat conduction properties, and have necessarily different geometries (since one is a thin deposited film while the other is a diffused region in the mono-crystalline silicon), the two resistors could still be maintained at a substantially same temperature, because of the greater thermal conduction and greater thermal inertia of the mono-crystalline mass. This principle can be extended to more than two resistors, since it is the entire micro-platform which feels the better temperature uniformity, and since the better temperature uniformity is delivered by the silicon island with less consideration of layout symmetry of the components on the island. Additional advantage can be gained from further positioning the resistors roughly symmetrically with respect to the heat source on the micro-platform.

The enhanced thermal uniformity also allows improvement in the trimming performance of thermally-trimmable resistors (and any other thermally-trimmable components), which are positioned in such a thermally-isolated island. For example, this is because for thermal trimming of resistors, typically the trimming direction and amount are sensitive functions of temperature and thermal history. WO2004/097859, also hereby incorporated by reference, describes how thermally-trimmable resistors can be trimmed bi-directionally. The technique described therein can be used with the present invention. If one substantial portion of the resistor is at a temperature slightly different from a neighboring portion, it may trim in the opposite direction from the neighboring portion, thus canceling the effect of the trim. Moreover, the thermal history of those two portions will now be different, leading to less predictability in the trimming algorithms.

Furthermore, the present invention also allows thermal trimming of the temperature coefficient of certain thermally-mutable resistors. Again the benefits of better temperature uniformity apply to the trimming of temperature coefficients (relative and/or absolute).

Following the ideas in the above paragraphs, the present invention also allows trimming of the temperature coefficient of a thermally-trimmable resistor to match or intentionally mismatch that of a diffused resistor (as described in WO2004/097860, WO2004/083840 and WO2004/097859). If one of the two resistors is not trimmable, one can trim the other's TCR to match it.

Figure 3A:
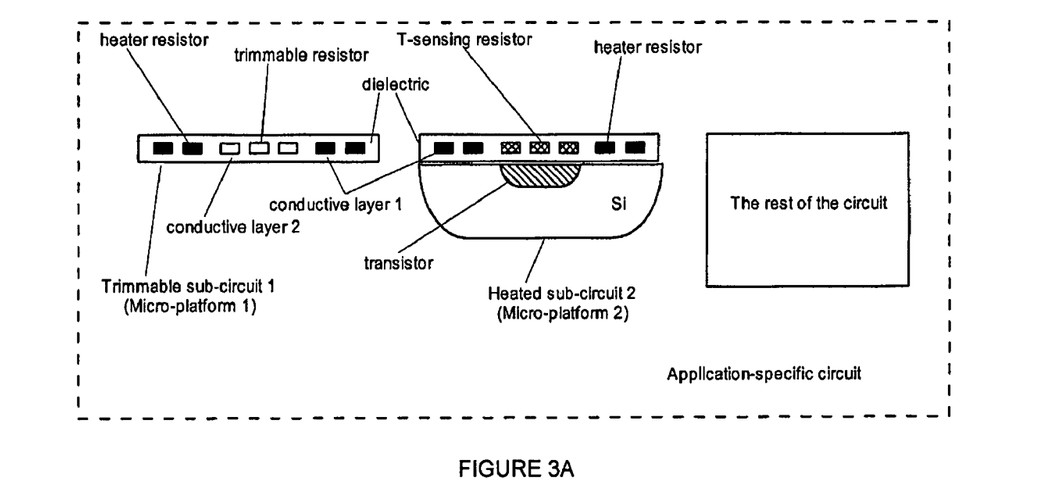
FIG. 3a shows an example of an application-specific circuit which includes a trimmable sub-circuit-1, positioned on a micro-platform without the mono-crystalline silicon portion, and sub-circuit-2, to be heated, but not trimmed, positioned on a micro-platform with a hanging mono-crystalline silicon portion.
Figure 3B:
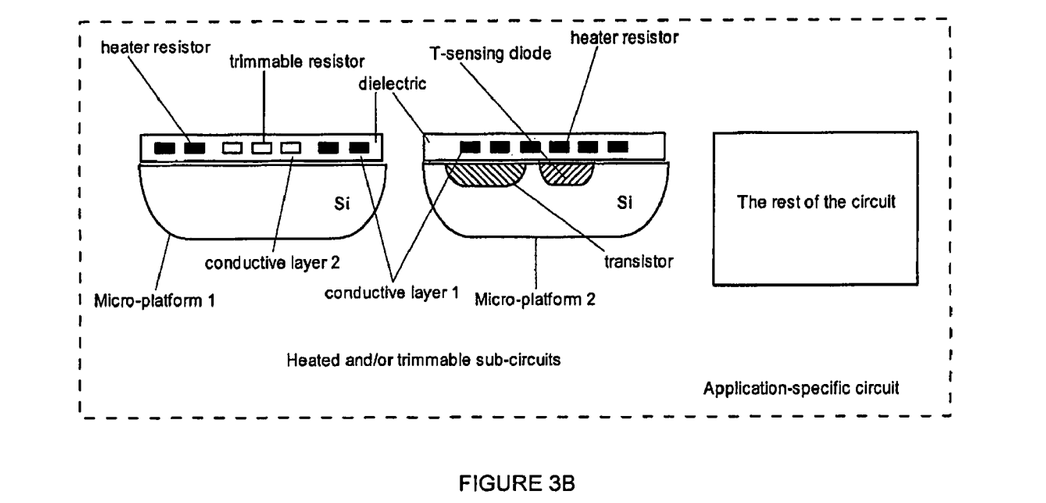
FIG. 3b shows another example of an application-specific circuit which includes a trimmable sub-circuit-1 and sub-circuit-2, where both are positioned on a micro-platform with a hanging mono-crystalline silicon portion, and both may be heated and/or trimmed.

Active Devices on a Silicon Island: The suspended silicon islands are suitable for housing of active silicon integrated devices or circuits, such as diodes, transistors, op-amps or voltage references, as illustrated in FIGS. 3a and 3b. These devices can be defined (created) in the (to-be-released) silicon during a host integrated circuit process which would be executed prior to the release etch. Such active devices housed on the island can be electrically connected to other devices on the chip through conductors embedded in or on the microstructure support arms.

Along with or without the active device(s), heater-resistors and (optionally) temperature sensors can also be housed on the same silicon island, in order to heat the island and measure the temperature on the island. Since the mono-crystalline silicon mass is an effective thermal conductor, it will act to make the temperature distribution uniform throughout the island.

A thermally-isolated island is well suited for measuring the absolute tempco of a circuit output, or component, parameter, etc, simply because one can readily embed a stable temperature sensor (one or more) in the island as part of most typical host semiconductor processes. Since the silicon island acts as a very good thermal conductor, the temperature will be relatively uniform, even if the heater(s) is(are) non-symmetrically placed on the island. Of course, it is best to design the heater(s) such that the temperature distribution is spatially constant. This needs only (1) a thermally-isolated island; (2) a heater, which can be for example a polysilicon resistor (which need not be particularly stable over time and use); (3) a device which can be calibrated and is stable enough to measure temperature on the island. This could be for example a stable (non-trimmable) resistor material, or a pn-junction-based temperature sensor.

With measurement of absolute tempco of a device (or parameter, etc.), you can also obtain relative tempco measurement of two or more devices on the island, without severe requirements on symmetry. Even if a stable accurate measurement of temperature is not available, the relative tempco of a circuit device/output/parameter is still available, simply by using an on-island heater to heat the island and the devices on it to a given temperature. Zero-crossing TCR is also available, in the same way as in WO 2004/097860, WO2004/083840.

Thermally-Trimmable Device on a Silicon Island: With a thermally-trimmable resistor in a circuit (not necessarily all thermally-isolated), one can make a thermally-trimmable circuit. The thermally-trimmable resistor (and perhaps parts of the circuit as well) can be located on the island. But with substantially the entire circuit located on the thermally-isolated island, one can also measure absolute or relative tempco of the circuit (or parts of it), and therefore use the trimmable resistor to trim the temperature behavior of the overall circuit (e.g. an output of the circuit).

Also, one need not trim only resistors, one can also use the high temperatures available from a heater-resistor in a thermally-isolated island to thermally anneal active devices (e.g. a diffused resistor, or diode or transistor characteristics), to trim their performance.

Tempco Matching and Conditioning of a Diffused Resistor in a Silicon Island: A resistor in the bulk of the silicon crystal (called a "diffused resistor), is typically made by incorporating the dopant into the silicon by ion implantation or by diffusion from films deposited on the surface of the wafer. For typical semiconductor process doping levels ($10^{15}/cm^3$ to $10^{19}/cm^3$), such diffused resistors typically have positive TCR. The resistivity of diffused resistors, for non-compensated extrinsic doping of either n-type or p-type, is given by the simple formula $\rho=1/[$(the electronic charge constant)* (carrier mobility)*(carrier concentration)]. Since, for extrinsic doping, the carrier concentration is roughly constant with temperature at temperatures within a few hundred degrees C of room temperature, the TCR is determined primarily by changes in the carrier mobility. As the temperature rises, the carrier mobility naturally decreases, giving an increased resistivity (positive TCR).

A variety of TCR's, including positive TCR's of up to several thousand ppm/K, are available in resistors made from thin film materials such as polysilicon. These films having substantial positive TCR's may be TCR-matched to diffused resistors. A heater positioned on the island such that the temperature is substantially the same at the polysilicon resistor and diffused resistor, would allow measurement of relative tempco of the two resistors, and thus allow trimming of the resistance and/or TCR of the thermally-trimmable material to match (or intentionally mismatch) the diffused resistor.

Furthermore, since the heater can reach temperatures in the neighborhood of 1000° C., this can cause diffusion of dopants in the silicon. Thus, the resistance of a resistor, optionally composed of one or more diffused regions embedded in a silicon island, may be trimmed in this way. The TCR of the diffused resistor may also be trimmed in this way.

Temperature-Conditionable Integrated Component(s) and/or Circuit on at Least one Silicon Island: The silicon island may contain integrated components, even an entire integrated circuit (or sub-circuit of a larger electronic system). For example, one may design certain critical components (active and/or passive) of a circuit to be on a silicon island (perhaps because the entire circuit may be too large to fit practically on an island). This circuit may include thermally-trimmable resistors.

The particular component(s) positioned on silicon islands may be thus positioned for measurement of tempco, or for their thermal trimming. It can be measurement of its/their own tempco, or for measurement of the influence of its/their temperature variation on an overall circuit output.

Note that the circuit may include several islands, which may all be in the same cavity or in separate cavities, and in each cavity there may be more than one island, and on each island there can be one, or more than one, component.

For example, if the goal is to temperature-condition an integrated voltage reference, one may place temperature-sensitive ("heat-critical") components on an island, along with a heater and temperature sensor, such that they may be heated to an appropriate temperature, for measurement of the influence of temperature variation on the overall circuit output. One may also place trimmable resistors on a separate micro-platform, with or without silicon mass, in the same cavity or a separate one, in order to trim to compensate for temperature-induced drifts in the overall circuit output.

In the case of certain voltage reference circuits, one can change the temperature coefficient of the output by trimming resistance. In such a case, it is not necessary that the temperature-sensitive component(s) (and its associated temperature-sensing element), be exposed to the high temperatures required for trimming resistance. It also may or may not be necessary (for example, depending on whether one prefers thermal uniformity to rapid trim times), that the thermally-trimmable resistor(s) have mono-crystalline silicon islands in the micro-platform, as shown in FIGS. 3A and 3B.

FIG. 3A shows a first micro-platform, where a trimmable sub-circuit is embedded. This trimmable sub-circuit could include a single thermally trimmable resistor, a combination of a resistor and one or more other components, or only one or more components. For this sub-circuit, the silicon mass underneath the micro-platform is not necessary. A second micro-platform, including the silicon mass, is also provided (above the same cavity or another cavity). It can house the same types of components as in the first micro-platform, plus devices which may be embedded in the mono-crystalline mass. This type of arrangement is useful in cases such as for example where one wants to place "heat-critical" active component(s) of a circuit on micro-platform-2, and heat it/them to a predetermined temperature in order to measure the impact on an overall circuit output, and then use the trimmable components on micro-platform-1 in order to trim the overall circuit to compensate the overall circuit output against temperature-induced variations caused by said "heat-critical" component (e.g. the case of trimming a voltage reference). The trimmable components on micro-platform-1 may not need the silicon mass, while the measurable components on micro-platform-2 may not need to feel the very high trimming temperatures. The remainder of the circuit shown in FIG. 3A forms the rest of the application specific circuit. FIG. 3B is a second embodiment, where both micro-platforms are suitable for heating and trimming, and include the silicon mass.

In general, in some cases it may be advantageous to position measure-only components on one or more thermally-isolated islands, and to-be-trimmed components on another island, (some of which may not have suspended mono-crystalline masses) (see FIG. 3).

As another example of the application of this invention in precision analog circuitry, a trimmable resistor can be a part of a current source which can be a part of a larger circuit. Such a current source could have the purpose, for example, of regulating the base current for a transistor. The value of that resistor can be fine-tuned by thermal trimming. Of course, its tempco may also be very important in maintaining the temperature stability of the circuit. The tempco of that resistor could be trimmed to a value at or near to zero, or intentionally to a non-zero value to compensate for temperature-induced variations in the function of the (active) device which is driven by the current source. Therefore, thermal trimming of both the resistance value and the tempco of that resistor may also be very important for overall circuit function. In this way, the trimmable resistor can be important in regulating the operation of an active device. In this case, one may place the trimmable resistor on a separate micro-platform from the active device. The temperature of both could be raised to equal temperatures, thus enabling calculation/estimation of the impact of temperature variation, and then the trimmable resistor could be trimmed to modify the temperature variation (to zero or to some other desired amount).

Another possible configuration for devices is shown in FIG. 4. There can be thermally-trimmable devices on each of the islands, positioned symmetrically around a central microstructure, on which there may be a heater to symmetrically heat the two adjacent islands.

Active silicon devices such as p-n junctions, diodes and transistors, are generally formed by diffusing dopants into a silicon substrate. The positions of these dopant profiles sensitively influence the properties and performance of the active devices in which they are positioned. Those positions are in part determined by the thermal budget which the dopants experience after their implantation or pre-deposition into the silicon surface. (Other factors influencing those dopant positions are mask geometry, implant energy and dose, and starting material, but in this context there is no opportunity to change these, once the process is completed.) The invented method can be used to fine-tune the thermal budgets of certain implanted dopant profiles by localized annealing of specific components, using such thermally-isolated silicon islands. Of course, it is advantageous that in this way one can tailor the anneal to a particular device, without affecting or degrading other circuit components integrated on the same chip. Since temperatures up to 1000° C. are available, with thermal inertia far less than that of a silicon wafer, it is possible to fine-tune the thermal budget much more precisely than even what is available in a rapid-thermal-annealing instrument.

In the case where one wants to anneal silicon devices at high temperatures, it is important to note that if there are metals or other conductors present on the island, they must be compatible with the thermal exposure anticipated during trimming. For example one way to avoid such a problem would be to use very-highly doped polysilicon having low sheet resistance (and relatively wide lines) for interconnection to and from the devices positioned on the islands.

Figure 5:
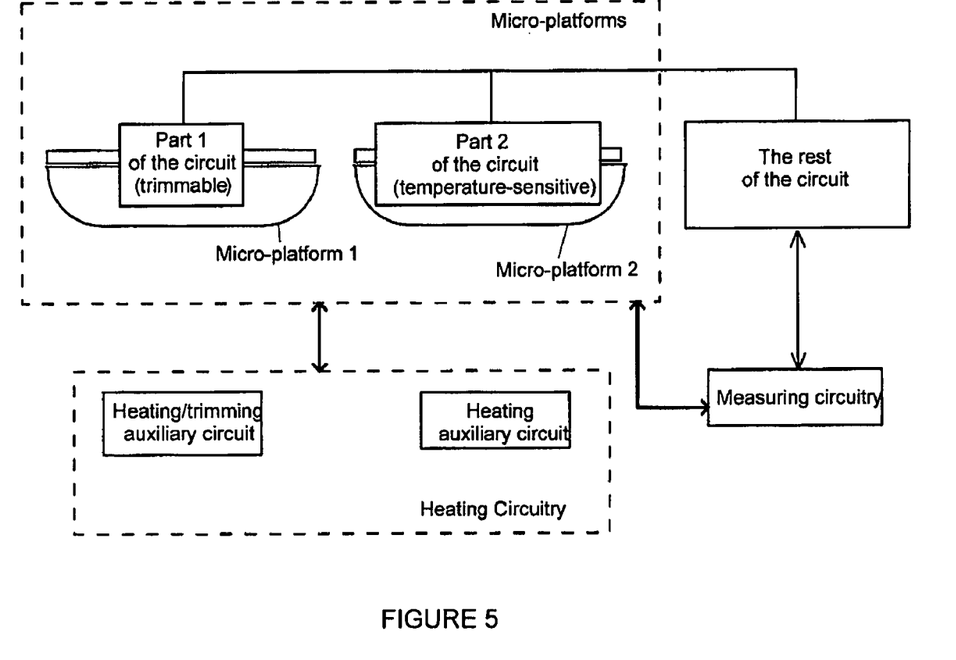
FIG. 5 is a block diagram of a circuit including the micro-platforms, heating circuitry, and measuring circuitry.

FIG. 5 illustrates one of many possible embodiments showing how the functional parts of the circuit can be embedded on two micro-platforms. Adjustable (trimmable) components are included in "Part 1" and located on a specially designed micro-platform 1. A temperature-sensitive part of the whole circuit (non-trimmable) is placed on micro-platform 2. The rest of the circuit can be placed elsewhere (on the same IC chip and/or even outside the chip). Measuring circuitry measures parameters of interest of the whole circuit. Heating circuitry generates electric pulses to heat locally temperature sensitive parts of the circuit and to measure temperature drift of the parameter of interest Electric pulses with higher amplitudes are applied to certain trimmable components to adjust/trim the whole circuit.

Calibration of the circuit may include repeated (depending on the application) cycles of the following sequence: measurement of parameter(s) of interest of the circuit; local heating of parts 1 and 2 of the circuit (separate or in parallel) with simultaneous measurement of the parameter of interest, by using heating circuitry, in order to measure temperature drift of the parameter of interest; trimming of trimmable component(s), by using the auxiliary trimming circuit (part of heating circuitry).

The embodiment(s) of the invention described above is(are) intended to be exemplary only. The scope of the invention is therefore intended to be limited solely by the scope of the appended claims

The invention claimed is:

1. A method of compensating for temperature variations in a temperature-sensitive portion of a circuit, the method comprising:

embedding said temperature-sensitive portion of said circuit in a suspended mass of mono-crystalline silicon beneath a thermally-isolated micro-platform on a substrate;

temperature conditioning said circuit by measuring an output of said circuit while unheated, heating said temperature-sensitive portion to imitate heating of said circuit, thereby causing temperature variations in said temperature-sensitive portion, and measuring said output of said circuit during said heating, determining a temperature drift of said circuit due to said heating;

calculating a desired trim of said circuit to compensate for said temperature drift; and trimming a part of said circuit.

2. A method as claimed in claim 1, wherein said heating comprises applying a heat pulse to a resistor embedded in said micro-platform.

3. A method as claimed in claim 1, wherein said trimming a part of said circuit comprises trimming a resistor embedded in said micro-platform.

4. A method as claimed in claim 1, wherein said trimming comprises applying local heat pulses to a component in the circuit, measuring a parameter, and repeating the applying until a desired value for the parameter has been reached.

5. A method as claimed in claim 4, wherein said parameter is a temperature coefficient of resistance.

6. A method as claimed in claim 4, wherein said parameter is an output of the circuit.

7. A method as claimed in claim 4, wherein said parameter is a relative temperature coefficient of resistance between a pair of resistors embedded in said micro-platform.

8. A method as claimed in claim 4, wherein thermally trimmable resistors are embedded in a first micro-platform, and non-trimmable components are embedded in a second micro-platform.

* * * * *